United States Patent
Dae et al.

(10) Patent No.: US 9,180,236 B2
(45) Date of Patent: *Nov. 10, 2015

(54) INTRA-AORTIC BALLOON COUNTERPULSATION WITH CONCURRENT HYPOTHERMIA

(71) Applicant: ZOLL Circulation, Inc., Sunnyvale, CA (US)

(72) Inventors: Michael W. Dae, Belmont, CA (US); Timothy R. Machold, Moss Beach, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 13/872,984

(22) Filed: Apr. 29, 2013

(65) Prior Publication Data

US 2013/0310632 A1    Nov. 21, 2013

Related U.S. Application Data

(60) Continuation of application No. 13/160,285, filed on Jun. 14, 2011, now Pat. No. 8,430,899, which is a division of application No. 10/933,970, filed on Sep. 2, 2004, now Pat. No. 7,959,643, which is a division of application No. 10/015,220, filed on Oct. 26, 2001, now Pat. No. 6,800,068.

(51) Int. Cl.
*A61F 7/00* (2006.01)
*A61M 1/10* (2006.01)
(Continued)

(52) U.S. Cl.
CPC .............. *A61M 1/1072* (2013.01); *A61F 7/123* (2013.01); *A61F 7/10* (2013.01);
(Continued)

(58) Field of Classification Search
USPC ........ 600/16–18; 604/94.01, 96.01, 106, 113, 604/291, 500, 509; 606/22, 25, 27, 28, 31, 606/192–194; 607/96, 104–106, 113; 128/898
See application file for complete search history.

(56) References Cited

U.S. PATENT DOCUMENTS 3,425,419 A    2/1969   Dato
4,111,209 A    9/1978   Wolvek et al.
(Continued)

FOREIGN PATENT DOCUMENTS

JP    2000-500364 A    1/2000
JP    2001-517966 A    10/2001
(Continued)

OTHER PUBLICATIONS

Moriyama et al. "Succesful Application of Hypothermia Combined with Intra-Aortic Balloon Pump Support to IOW-Cardiac-Output State After Open Heart Surgery". vol. 47, Jun. 1996, pp. 594-599.

*Primary Examiner* — Aaron Roane
(74) *Attorney, Agent, or Firm* — Robert D. Buyan; Stout, Uxa & Buyan, LLP

(57) ABSTRACT

Devices, systems and methods for treating disorders characterized by low cardiac output. The devices, systems and methods use intra-aortic balloon counterpulsation in combination with hypothermia of all or a portion of a human or veterinary patient's body to improve coronary perfusion and cardiac output. To effect the hypothermia, a heat exchange catheter may be positioned in the a patient's vasculature separately from the intra-aortic balloon counterpulsation catheter. Alternatively, a combination Intra-aortic balloon counterpulsation/heat exchange catheter may be utilized. Such combination catheter comprises a) a catheter sized for insertion into the aorta, b) a counterpulsation balloon and c) a heat exchanger. A drive/control system receives temperature and electrocardiograph signals and drives the inflation/deflation of the counterpulsation balloon as well as the heating/cooling of the heat exchanger.

17 Claims, 4 Drawing Sheets

(51) Int. Cl.
*A61F 7/12* (2006.01)
*A61F 7/10* (2006.01)
*A61M 19/00* (2006.01)

(52) U.S. Cl.
CPC  *A61F 2007/0056* (2013.01); *A61F 2007/0095* (2013.01); *A61F 2007/126* (2013.01); *A61M 19/00* (2013.01); *A61M 2205/3606* (2013.01)

(56) References Cited

U.S. PATENT DOCUMENTS

| | | | |
|---|---|---|---|
| 4,762,130 | A | 8/1988 | Fogarty et al. |
| 5,106,360 | A | 4/1992 | Ishiwara et al. |
| 5,151,100 | A | 9/1992 | Abele et al. |
| 5,211,631 | A | 5/1993 | Sheaff |
| 5,417,653 | A | 5/1995 | Sahota et al. |
| 5,486,208 | A | 1/1996 | Ginsburg |
| 5,531,776 | A | 7/1996 | Ward et al. |
| 5,624,392 | A | 4/1997 | Saab |
| 5,716,386 | A | 2/1998 | Ward et al. |
| 5,837,003 | A | 11/1998 | Ginsburg |
| 5,865,721 | A | 2/1999 | Andrews et al. |
| 5,957,963 | A | 9/1999 | Dobak, III |
| 5,971,979 | A | 10/1999 | Joye et al. |
| 6,019,783 | A | 2/2000 | Philips et al. |
| 6,033,383 | A | 3/2000 | Ginsburg |
| 6,042,559 | A | 3/2000 | Dobak, III |
| 6,051,019 | A | 4/2000 | Dobak, III |
| 6,071,956 | A | 6/2000 | Slepian et al. |
| 6,096,068 | A | 8/2000 | Dobak, III et al. |
| 6,110,168 | A | 8/2000 | Ginsburg |
| 6,126,684 | A | 10/2000 | Gobin et al. |
| 6,146,411 | A | 11/2000 | Noda et al. |
| 6,149,670 | A | 11/2000 | Worthen et al. |
| 6,190,304 | B1 | 2/2001 | Downey et al. |
| 6,224,624 | B1 | 5/2001 | Lasheras et al. |
| 6,231,594 | B1 | 5/2001 | Dae |
| 6,238,428 | B1 | 5/2001 | Werneth et al. |
| 6,245,095 | B1 | 6/2001 | Dobak, III et al. |
| 6,251,129 | B1 | 6/2001 | Dobak, III et al. |
| 6,261,312 | B1 | 7/2001 | Dobak, III et al. |
| 6,264,679 | B1 | 7/2001 | Keller et al. |
| 6,283,959 | B1 | 9/2001 | Lalonde et al. |
| 6,287,326 | B1 | 9/2001 | Pecor |
| 6,290,717 | B1 | 9/2001 | Philips |
| 6,299,599 | B1 | 10/2001 | Pham et al. |
| 6,312,452 | B1 | 11/2001 | Dobak, III et al. |
| 6,338,727 | B1 | 1/2002 | Noda et al. |
| 6,393,320 | B2 | 5/2002 | Lasersohn et al. |
| 6,405,080 | B1 | 6/2002 | Lasersohn et al. |
| 6,497,721 | B2 | 12/2002 | Ginsburg et al. |
| 6,516,224 | B2 | 2/2003 | Lasersohn et al. |
| 6,554,797 | B1 | 4/2003 | Worthen |
| 6,645,233 | B1 | 11/2003 | Ayers et al. |
| 7,144,407 | B1 | 12/2006 | Lasersohn |
| 2001/0041923 | A1 | 11/2001 | Dobak, III |

FOREIGN PATENT DOCUMENTS

| | | |
|---|---|---|
| WO | WO 97/18005 A1 | 5/1997 |
| WO | WO 97/25011 A1 | 7/1997 |
| WO | WO 00/09054 A1 | 2/2000 |
| WO | WO 00/10494 A1 | 3/2000 |
| WO | WO 00/48670 A1 | 8/2000 |
| WO | WO 00/66053 A1 | 11/2000 |
| WO | WO 01/13809 A1 | 3/2001 |

INTRA-AORTIC BALLOON COUNTERPULSATION WITH CONCURRENT HYPOTHERMIA

RELATED APPLICATIONS

This patent application is a continuation of copending U.S. patent application Ser. No. 13/160,285 filed Jun. 14, 2011, which is a division of U.S. patent application Ser. No. 10/933,970 filed Sep. 2, 2004 and issued as U.S. Pat. No. 7,959,643 on Jun. 14, 2011, which is a division of U.S. patent application Ser. No. 10/015,220 filed Oct. 26, 2001 and issued as U.S. Pat. No. 6,800,068 on Oct. 5, 2004, the entire disclosure of each such patent and application being expressly incorporated herein by reference.

FIELD OF THE INVENTION

This invention relates generally to methods and apparatus for medical treatment and more particularly to methods, devices and systems for administering intra-aortic balloon counterpulsation concurrently with the use of a heat exchange catheter for inducing and maintaining hypothermia in at least a portion of the patient's body (e.g., cardiac hypothermia, cardiac & cerebral hypothermia, etc.)

BACKGROUND OF THE INVENTION

A. Intra-Aortic Balloon Pump (IABP) Counterpulsation

An intra-aortic balloon pump (IABP) is a device that may be used to a) increase myocardial blood flow in patients whose cardiac output is compromised due to heart failure or cardiac insufficiency and b) decreases the heart's workload, through a process called counterpulsation.

During each cardiac cycle, the human heart expels oxygenated blood into the aorta as its left ventricle contracts (i.e., during systole) and, thereafter, receives a backflow of arterial blood into the coronary arteries as its left ventricle relaxes (i.e., during diastole). The systolic pumping of blood into the aorta requires the heart muscle to overcome the static pressure of blood that is already in the aorta. A healthy heart is typically able to perform both of these functions effectively. However, a weakened or failing heart may be unable to perform the work required to fully overcome the static pressure of blood already in the aorta, thereby resulting in less ejection of oxygenated blood into the aorta during systole and less backflow of oxygenated blood into the coronary arteries during diastole. Intra-aortic balloon counterpulsation is a technique which causes more arterial blood to enter the coronary arteries (and thus more blood flow to the heart muscle) during diastole (less flow work) and decreases the amount of work that the heart must perform during systole (less pressure work). By increasing coronary blood flow, the myocardium receives more oxygen, thereby allowing the heart to pump more effectively and increasing the cardiac output that occurs with each heartbeat (i.e., the "stroke volume").

The IABP comprises a) a balloon catheter that is percutaneously insertable into the patient's aorta and b) a control console that is attached to the balloon catheter. A computer or controller within the control console receives the patient's electrocardiogram (ECG). In response to the ECG signal, the controller causes the intra-aortic balloon to be inflated during diastole (when the heart muscle relaxed) resulting in increased back pressure within the aorta and increased blood flow into the coronary arteries, and deflated during early systole (during a phase known as "isometric contraction") resulting in a reduction of intra-aortic pressure against which the heart must pump. In this way, the IABP improves blood flow to the heart muscle and reduces the workload of the heart muscle. Additionally, IABP counterpulsation has been demonstrated to improve peripheral or systemic arterial perfusion. Although the mechanism by which IABP counterpulsation improves peripheral or systemic profusion is not well understood, it is believed that inflation of the intra-aortic balloon during diastole serves to facilitate peripheral runoff (sometimes referred to as the intrinsic "Windkessel" effect) which then augments peripheral perfusion.

Preferably, the gas used to inflate the balloon is either carbon dioxide (which has fewer consequences in the rare event of a balloon bursting) or helium (which has the fastest ability to travel or diffuse).

B. The Effects of Hypothermia on Cardiac Function

Mild hypothermia has been shown to both increase the contractility of the heart muscle and to reduce its metabolic requirements. Indeed, if the hypothermia is systemic, the metabolic demands of the entire body are generally reduced, so that the demands placed on the heart may be reduced. Additionally, when the patient's body temperature is reduced and maintained 1EC or more below normothermic (e.g., less than 36EC in most individuals), such that the output of the heart increases, the condition and function of the heart muscle may improve significantly due to the combined effects of increased bloodflow to the heart, a temporarily decreased metabolic need and decreased metabolic waste products.

One method for inducing hypothermia of the heart or entire body is through the use of a heat exchange catheter that is inserted into a blood vessel and used to cool blood flowing through that blood vessel. This method in general is described in U.S. Pat. No. 6,110,168 to Ginsburg, which is expressly incorporated herein by reference. Various heat exchange catheters useable for achieving the endovascular cooling are described in U.S. Pat. No. 5,486,208 (Ginsburg), PCT International Publication WO 00/10494 (Machold et al.), U.S. Pat. No. 6,264,679 (Keller et al.), U.S. patent application Ser. No. 09/777,612, all of which are expressly incorporated herein by reference. Other endovascular cooling catheters may be employed to practice this patented method, for example U.S. Pat. No. 3,425,484 (Dato), U.S. Pat. No. 5,957,963 (Dobak III) and U.S. Pat. No. 6,126,684 (Gobin, et al.), provided that they are able to provide adequate hypothermia to the diseased heart.

The potential for shivering is present whenever a patient is cooled below that patient's shivering threshold, which in humans is generally about 35.5° C. When inducing hypothermia below the shivering threshold, it is very important to avoid or limit the shivering response. The avoidance or limiting of the shivering response may be particularly important in patients who suffer from compromised cardiac function and/or metabolic irregularities. An anti-shivering treatment may be administered to prevent or deter shivering. Examples of effective anti-shivering treatments are described in U.S. Pat. No. 6,231,594 (Dae et al.).

SUMMARY OF THE INVENTION

The present invention provides a catheter device that is insertable into the aorta of a human or veterinary patient. Such catheter device comprises a) a balloon that is useable for performing intra-aortic counterpulsation and b) a heat exchanger for exchanging heat with the patient's flowing blood so as to induce hypothermia of all or a portion of the patient's body.

Further in accordance with the invention, the catheter device of the foregoing character may be used in combination with driving and control apparatus connected to the catheter for a) causing and controlling the inflation/deflation of the intra-aortic balloon and b) cool or warming the heat exchanger to bring about and maintain the desired hypothermia of all or a portion of the patient's body. The driving and control apparatus may be positioned extracorporeally and may be housed in one or more consoles that are positioned near the patient's bed. Preferably, at least the patient's heart (and in some cases the brain, other portions of the body or the entire body) will be maintained at a temperature 1EC or more below normothermic (e.g., less than 36EC in most humans).

Still further in accordance with the invention, the heat exchanger of the catheter device may comprise less than the entire length of the catheter.

Still further in accordance with the invention, the heat exchanger of the catheter may comprise or be associated with one or more flow-disrupting surface(s) which increase the effective heat exchange surface area and/or alter or disrupt the laminarity of blood flow adjacent to the heat exchanger in a manner that causes some turn over of blood within heat exchange proximity to the heat exchanger and a resultant increase in the efficiency of the heat exchange process.

Still further in accordance with the invention, the heat exchanger of the catheter may be of a flowing fluid type, wherein a fluidic heat exchange medium (e.g., saline solution) is circulated through the catheter and through the heat exchanger. In some embodiments, such flowing fluid type heat exchanger may comprise a flexible structure (e.g., a balloon) which expands or become taut when the heat exchange fluid is circulated therethrough. In some of these embodiments, the heat exchange balloon may be multi-lobed and/or may be curved or twisted (e.g., helical) in configuration. Also, in some embodiments which utilize the flowing fluid type heat exchanger, a wall or surface which separates the patient's flowing blood from the heat exchange medium being circulated through the heat exchanger may comprise a metal to provide for provide for improved heat transmission between the blood and the heat exchange medium.

Still further in accordance with the invention, in some embodiments the heat exchanger and the counterpulsation balloon may comprise one in the same structure. In this regard, the counterpulsation balloon may be inflated and deflated with a cold gas such that the counterpulsation balloon itself serves as a heat exchanger (in addition to performing its counterpulsation function). Alternatively, a channel or space for recirculation of heat exchange medium (e.g., cooled saline solution) may be formed on or in a wall or portion of the counterpulsation balloon such that heat exchange medium is circulated therethrough as the counterpulsation balloon undergoes repeated inflation and deflation.

Still further in accordance with the invention, in some embodiments, the heat exchanger may be located more distally on the catheter than the counterpulsation balloon, such that when the catheter is advanced in retrograde fashion into the patient's aorta to a position where the counterpulsation balloon is properly positioned to perform its counterpulsation function (e.g., within the thoracic aorta), the heat exchanger will be positioned superior to the counterpulsation balloon (e.g., within the aorta between the heart and the counterpulsation balloon).

Still further in accordance with the invention, in some embodiments, the heat exchanger may be located more proximally on the catheter than the counterpulsation balloon, such that when the catheter is advanced in retrograde fashion into the patient's aorta to a position where the counterpulsation balloon is properly positioned to perform its counterpulsation function (e.g., within the thoracic aorta), the heat exchanger will be located inferior to the counterpulsation balloon (e.g., within the aorta between the counterpulsation balloon and the iliac bifurcation.

Still further in accordance with the invention, the method may be carried out using separate intra-aortic balloon counterpulsation catheter and heat exchange catheters. In such two-catheter embodiments of the method, the heat exchange catheter is separate from the intra-aortic balloon counterpulsation catheter and thus need not necessarily be positioned in the aorta along with the intra-aortic balloon counterpulsation catheter. Rather, the separate heat exchange catheter may be positioned in any suitable blood vessel (vein or artery) to effect cooling of the desired portion of the patient's body and/or the entire patient's body. Examples of separate heat exchange catheters and related control systems are described in U.S. Pat. No. 5,486,208 (Ginsburg), U.S. Pat. No. 6,264, 679 (Keller et al.), U.S. Pat. No. 3,425,484 (Dato), U.S. Pat. No. 5,957,963 (Dobak III) U.S. Pat. No. 6,126,684 (Gobin, et al.), U.S. Pat. No. 6,264,679 (Keller et al.) and U.S. Pat. No. 5,531,776 (Ward et al.), as well as in PCT International Publication WO 00/10494 (Radiant Medical, Inc.) and copending U.S. patent application Ser. No. 09/777,612, the entireties of which are expressly incorporated herein by reference.

Still further in accordance with the invention, the method may further comprise the step of administering to the patient an anti-shivering treatment such as those described in U.S. Pat. No. 6,231,594 (Dae et al.), the entirety of which is expressly incorporated herein by reference.

Still further aspects and elements of the present invention will become apparent to those skilled in the art upon reading and considering the detailed descriptions of examples set forth herebelow and in the accompanying drawings.

BRIEF DESCRIPTION OF THE DRAWINGS

FIG. 1 is a diagram of a human body showing relevant portions of the cardiovascular system including the heart (H), aorta (A) and femoral artery (FA).

FIG. 2 is a cut-away view of the heart (H) and great vessels, showing the coronary arteries (CA), aortic arch (AA), brachiocephalic trunk (BCT), left common carotid artery (LCC) and left subclavian artery (LSA).

FIG. 3 is a schematic diagram of an intra-aortic balloon/heat exchanger catheter (10) of the present invention positioned within the aorta (A) and connected to driving/control apparatus (30) that control and operate the catheter's counterpulsation balloon (14) and heat exchanger (16).

FIG. 3a is a cut away view of portion 3a of FIG. 3, showing one example of the manner in which the heat exchanger 16 my be constructed.

FIG. 3b is a cross sectional view through line 3b-3b of FIG. 3.

FIG. 4 is a schematic diagram of the thoracic aorta of a human patient wherein an alternative embodiment of a balloon/heat exchanger catheter (10a) of the present invention is positioned.

FIG. 4b is an enlarged sectional view of the heat exchanger of the catheter (10b) shown in FIG. 4a.

DETAILED DESCRIPTION OF SPECIFIC EMBODIMENTS

Figure 1:
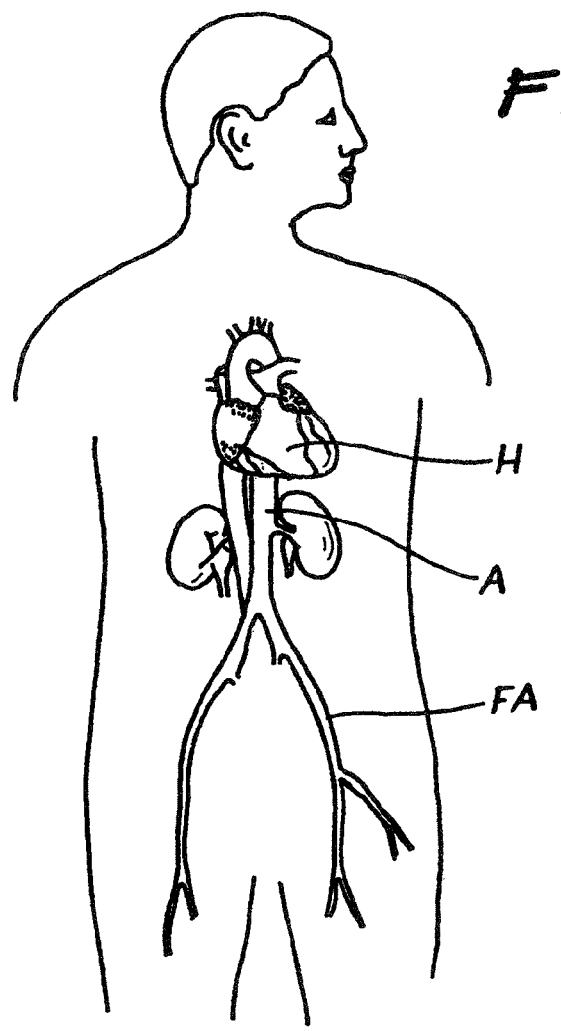
FIGS. 1-4b, attached hereto, show examples or embodiments of the methods and apparatus of the present invention, as follows.
Figure 2:
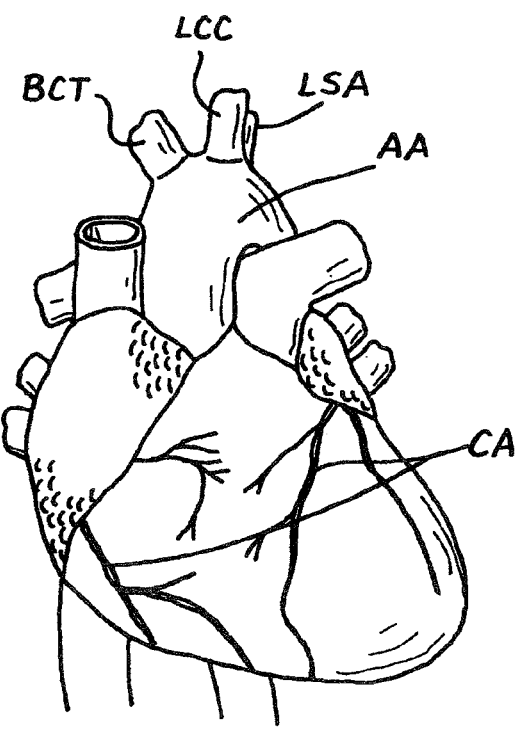

The following detailed description is provided for the purpose of describing only certain embodiments or examples of the invention and is not intended to describe all possible embodiments and examples of the invention.

With reference to FIGS. 1-4b, a balloon/heat exchanger catheter 10, 10a, 10b of the present invention generally comprises an elongate catheter body 12, 12a, 12b having a heat exchanger 16, 16a, 16b and a counterpulsation balloon 14, 14a, 14b positioned thereon. As may be seen from the cross-section of FIG. 3B, the catheter body 12, 12a, 12b proximal to the heat exchanger 16, 16a, 16b comprises a gas inflation/deflation lumen 52 through which gas or other suitable fluid is alternately infused and withdrawn to effect inflation and deflation of the counterpulsation balloon 14, 14a, 14b as well as heat exchange fluid inflow and outflow lumens 54, 56 through which heat exchange fluid is circulated through the heat exchanger 16, 16a, 16b. Preferably, the heat exchange fluid inflow lumen 54 is connected to the proximal end of the heat exchanger 16, 16a, 16b and the heat exchange fluid outflow lumen 56 is connected to the distal end of the heat exchanger 16, 16a, 16b, thereby causing the heat exchange fluid to flow through the heat exchanger 16, 16a, 16b in a direction opposite the direction in which blood is flowing through the patient's aorta.

Figure 3:
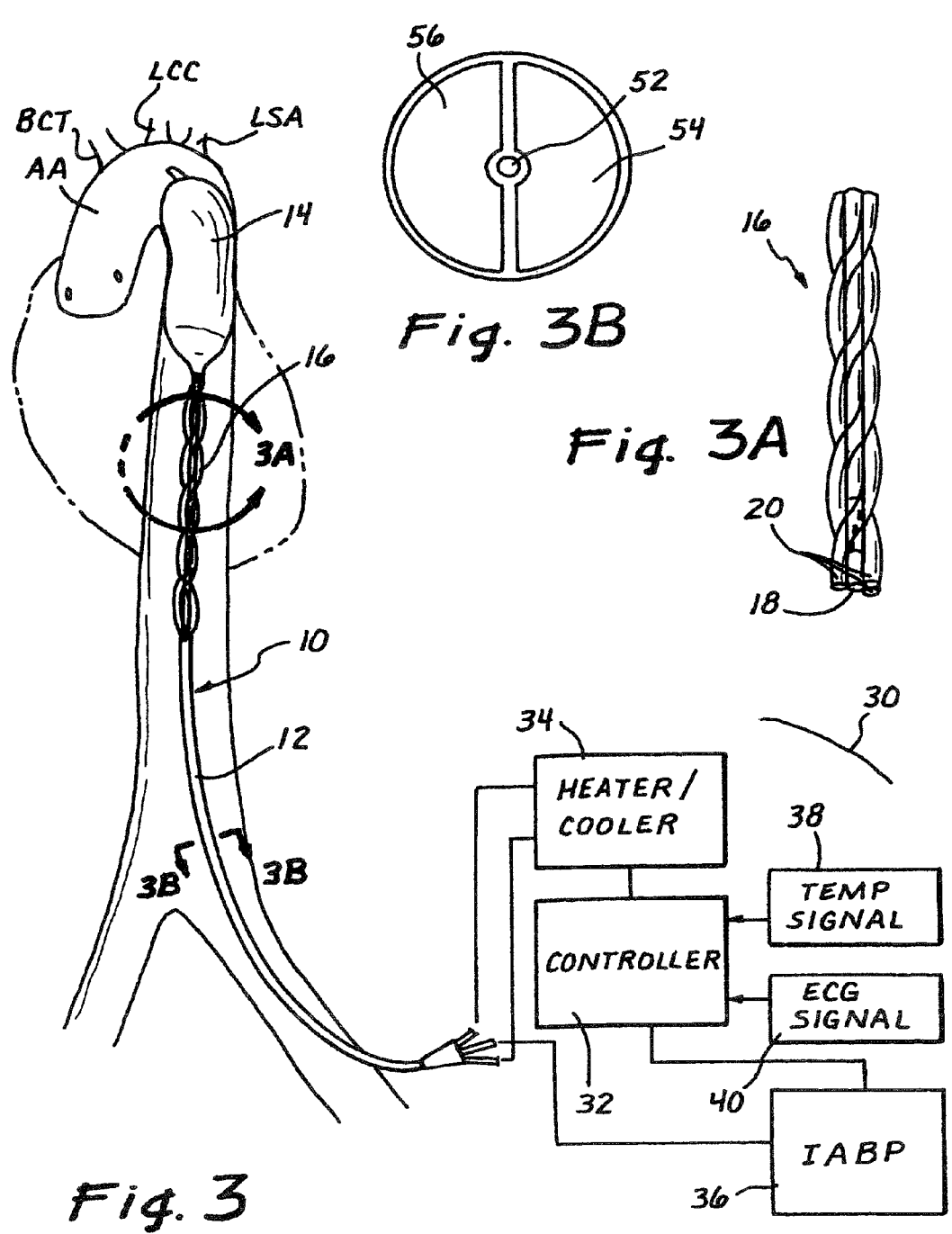

In some embodiments, such as that shown in FIG. 3, the counterpulsation balloon 14, may be positioned on a portion of the catheter body 12 that is distal to the heat exchanger 16. In other embodiments, such as those shown in FIGS. 4a and 4b, the counterpulsation balloon 14a, 14b may be positioned on a portion of the catheter body that is proximal to the heat exchanger 16a, 16b. Additionally, hybrids or combinations of these designs may also be employed wherein one or more heat exchangers may be positioned proximal and distal to the counterpulsation balloon.

The catheter body 12, 12a, 12b has multiple lumens as needed to permit the passage of balloon inflation fluid (e.g., carbon dioxide or helium) into and out of the counterpulsation balloon 14, 14a, 14b and the passage of energy or heated/cooled thermal exchange fluid into the heat exchanger 16, 16a, 16b. In this regard, the heat exchanger preferably comprises at least one heat exchange surface that is in contact with a heat exchange lumen through which a heated or cooled heat exchange medium (e.g., saline solution) may be passed. In the particular embodiments shown in the figures, the heat exchange surface comprises the blood-contacting outer surfaces of helical tubes 20 (FIGS. 3, 3a and 4) or straight tubes 48 through which the heat exchange medium is circulated. In other embodiments, not shown, the heat exchanger may comprises a thermoelectric element or chemically cooled member mounted within or on the catheter body and connected to the extracorporeal drive/control apparatus 30 by a wire or other communication pathway that extends through the catheter body 12 to deliver electrical current, chemical activators or other forms of energy to the heat exchanger for the purpose of causing the heat exchanger to warm and/or cool as needed to maintain the desired temperature.

The drive/control apparatus 30 is useable to drive and control the heat exchanger 16, 16a, 16b and the counterpulsation balloon 14, 14a, 14b. With respect to controlling and driving of the heat exchanger 16, 16a, 16b, the drive/control apparatus 30 comprises a heater/cooler 34 for causing the heat exchanger 16, 16a, 16b, to heat or cool as needed. Generally, the drive/control apparatus 30 comprises a controller 32 such as a microprocessor or computer, a heater/cooler 34 for heating and cooling the heat exchanger 16, 16a, 16b, a temperature monitoring apparatus for providing a temperature signal 38 to the controller 32 and an electrocardiogram (ECG) monitoring apparatus for providing an ECG signal to the controller 32.

Specific examples of the types of apparatus that comprise the heater/cooler 34 and the portions or function of the controller 32 that control the heat exchanger 16, 16a, 16b and temperature probes that provide the temperature signal 40 are described in the above-incorporated PCT International Publication WO OO/10494. It is presently preferred that the patient's esophageal temperature be measured by a temperature probe positioned in the esophagus and that the temperature signal received by the controller 32 receive a signal 40 indicative of such monitored esophageal temperature. A desired target temperature is set or inputted into the controller 32 and the controller 32 is programmed to cause the heater/cooler to heat or cool the heat exchanger 16, 16a, 16b to maintain the monitored temperature at or near the desired target temperature.

With respect to driving (e.g., inflating and deflating) and controlling of the counterpulsation balloon 14, 14a, 14b, the drive/control apparatus 30 comprises a pump (IABP) for pumping inflation fluid into and out of the counterpulsation balloon at specific times in relation to the cardiac cycle or ECG. Specific examples of the IABP and the other components/functions of the controller 32 used to drive and control the counterpulsation balloon 14, 14a, 14b and means for providing and processing the ECG signal 40 are described in U.S. Pat. No. 3,504,662 (Goetz et al.) and U.S. Pat. No. 3,504,662 (Jones), the entireties of which are expressly incorporated herein by reference.

Figure 4:
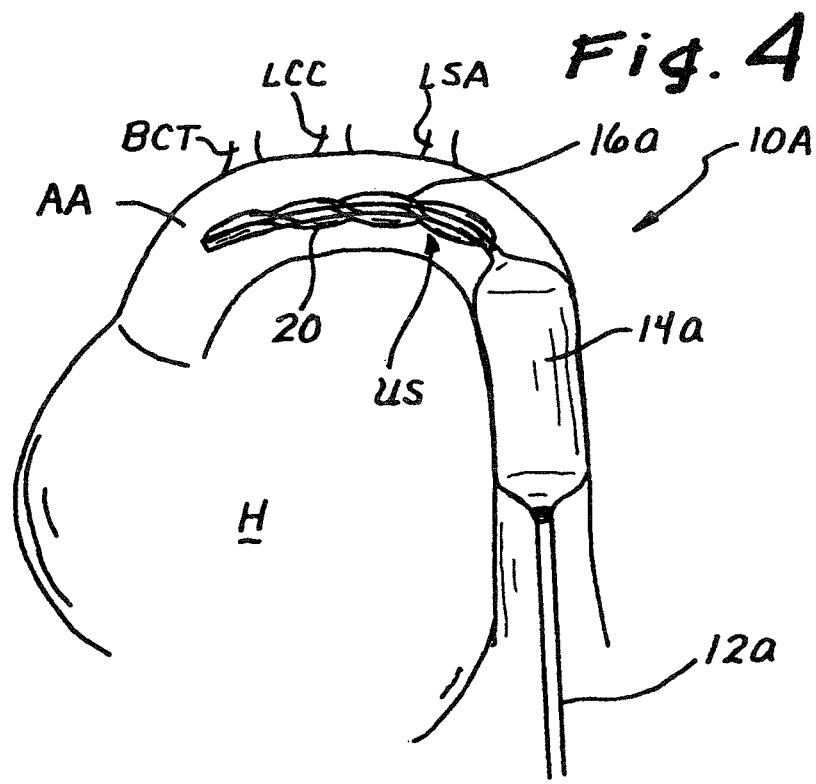
Figure 4A:
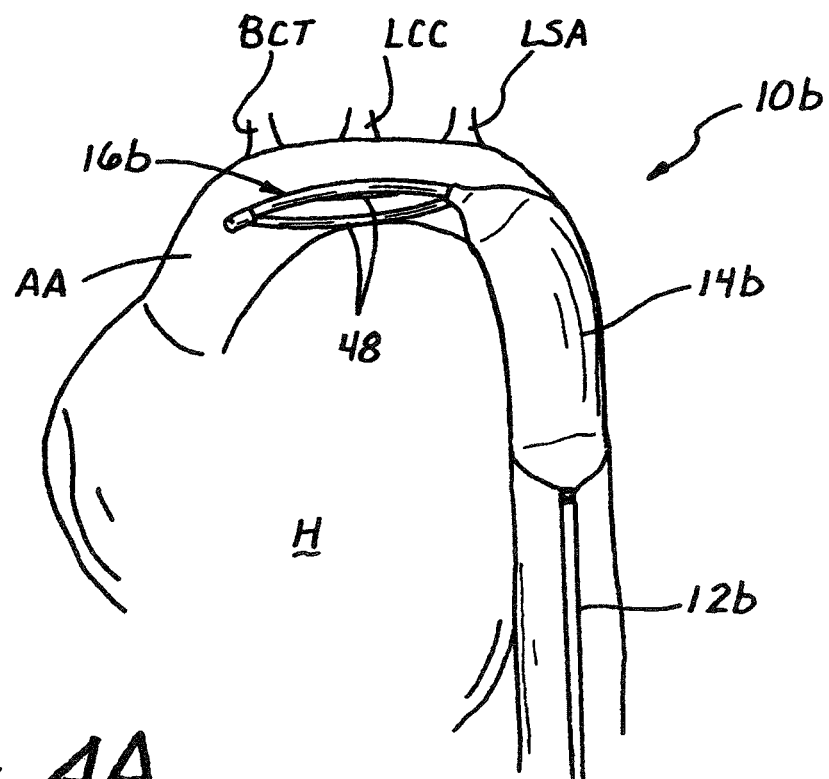
FIG. 4a is a schematic diagram of the thoracic aorta of a human patient wherein yet another alternative embodiment of a balloon/heat exchanger catheter (10a) of the present invention is positioned.
Figure 4B:
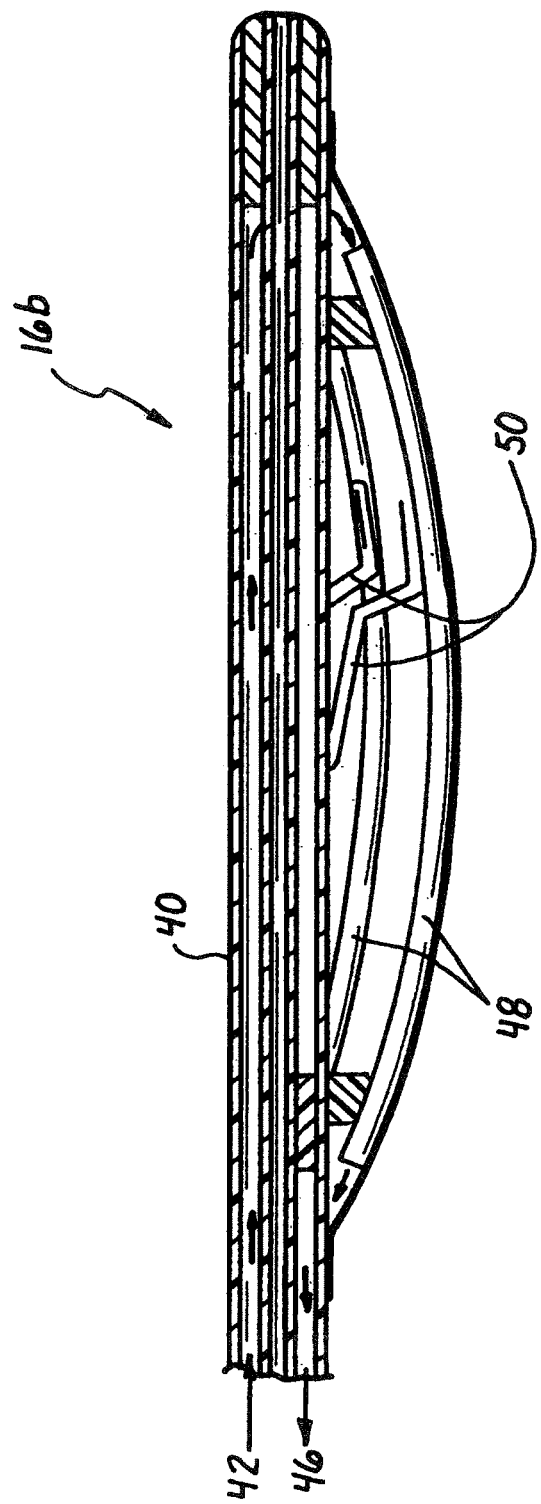

It will be appreciated that, in embodiments such as those shown in FIGS. 4-4b, wherein the heat exchanger 16a, 16b is located on the catheter distal to the counterpulsation balloon 14a, 14b, it may be necessary or desirable for the heat exchanger 16a, 16b to reside within the arch of the aorta AA in order for the counterpulsation balloon 14a, 14b to be optimally positioned within the thoraco-abdominal aorta A inferior to the left subclavian artery LSA, but still superior to other branches of the aorta such as the superior mesenteric and renal arteries. In such cases, it may be desirable to construct or utilize the heat exchanger 16a, 16b in a way that avoids blocking or disrupting flow into the coronary ostia CO, brachiocephalic trunk BCT, left common carotid artery LCA and/or left subclavian artery LSA. As shown in FIG. 4, this may be accomplished by simply causing the heat exchanger 16a to be smaller in diameter than the lumen of the aortic arch AA such that flow space exists around the heat exchanger 16 and the coronary ostia CO, brachiocephalic trunk BCT, left common carotid artery LCA and/or left subclavian artery LSA remain unobstructed. Another approach, as shown in FIGS. 4a-4b, is to construct the heat exchanger 16b such that its heat exchange elements 48, when fully deployed and operational, cannot obstruct or block the coronary ostia CO, brachiocephalic trunk BCT, left common carotid artery LCA and/or left subclavian artery LSA. In the particular embodiment shown in FIGS. 4a-4b, the distal portion of the catheter body 12b is preformed to a "J" shape and the heat exchanger 16b comprises a plurality of arcuate heat exchange tubes 48 that are disposed on the underside US of the J shaped catheter body 12 such that the heat exchange tubes 48 remain adjacent the wall of the aorta A that is opposite the brachiocephalic trunk BCT, left common carotid artery LCA and/or left subclavian artery LSA.

The cooling of the patient's body may cause some shivering to occur, if the patient's core body temperature is cooled to less than about 35.5EC. In such cases, it may be desirable to administer an anti-shivering treatment to prevent or lessen the shivering and enhance the patient's comfort. Such anti-shivering treatment may comprise the mere application of warmth to the patient's skin as may be accomplished by a warming blanket of the type commonly used in hospitals. Alternatively or additionally, such anti-shivering treatment may comprise the administration of drugs or agents to minimize or prevent the shivering response. Examples of agents that are useable for this purpose are described in the above-incorporated U.S. Pat. No. 6,231,594 (Dae et al.). For example, an anti-shivering treatment may comprise the steps of:

(i) administering an initial bolus dose of a first anti-thermoregulatory response agent to the patient (for example an oral dose of a serotonin 5 HT1a receptor agonist such as 60 mg of buspirone);

(ii) administering a subsequent dose of a second anti-thermoregulatory response agent to the patient (for example an initial intravenous dose of an μ opioid receptor agonist such as 50 mg of meperidine administered by slow push followed by a similar second dose); and (iii) administering a further dose of the second anti-thermoregulatory response agent by constant IV administration (for example, constant IV administration of about 25 mg/hr of meperidine).

Alternatively, another anti-shivering treatment that may be more suitable for longer term use (e.g., more than 24 hours) comprises the following steps:

(i) administering a first dose of an anti-thermoregulatory response agent to the patient (for example an intravenous dose of an μ opioid receptor agonist such as 50 mg of meperidine administered by slow push and infused over about 5 minutes);

(ii) administering a second dose of the anti-thermoregulatory response agent to the patient (for example, about 15 minutes after the initial administration of meperidine, an additional 50 mg of meperidine is administered by slow IV push);

(iii) administering a third dose of the anti-thermoregulatory response agent by constant IV administration (for example, constant IV administration of about 25 mg/hr of meperidine maintained for the duration of the time that the patient's temperature is below the shivering threshold);

(iv) an intravenous temperature control catheter of the general type described above is introduced into the vasculature of the patient and the heat exchange region of the catheter is placed in the IVC and cooling is begun at the maximum rate. The patient is thereafter maintained at a therapeutically low temperature even below the shivering threshold.

Another class of anti-shivering drugs that may be particularly useful are the alpha-adrenergic receptor agonists, such as dexmedetomidine and clonidine.

Although several illustrative examples of means for practicing the invention are described above, these examples are by no means exhaustive of all possible means for practicing the invention. For example, as described in the Summary of the Invention, instead of using a combination heat exchange/IABP catheter as shown in the drawings, a standard or conventional IABP catheter may be used and a separate heat exchange catheter may be deployed in the aorta or elsewhere, such as in the inferior vena cava or venous vasculature, to effect the desired cooling of the patient's heart, other body parts or entire body. Other modifications to the embodiment shown in the drawings are also possible. The scope of the invention should therefore be determined with reference to the appended claims, along with the full range of equivalents to which those claims are entitled.

What is claimed is:

1. A method for providing circulatory support while decreasing metabolic demand in a human or veterinary patient, said method comprising the steps of:
   a. providing a heat exchange catheter comprising i) a heat exchange catheter body and ii) at least one heat exchanger for exchanging heat with blood flowing through a blood vessel into which the heat exchange catheter body is inserted;
   b. providing an intra-aortic balloon counterpulsation catheter comprising i) a counterpulsation catheter body and ii) a counterpulsation balloon useable for effecting intra-aortic balloon counterpulsation;
   c. inserting the heat exchange catheter into the patient's vasculature such that blood flows in heat exchange proximity to the heat exchanger;
   d. inserting the intra-aortic balloon counterpulsation catheter into the patient's vasculature such that the counterpulsation balloon is positioned within the patient's aorta;
   e. using the intra-aortic balloon counterpulsation catheter to effect circulatory support by intra-aortic balloon counterpulsation; and,
   f. using the heat exchange catheter to cool the patient's body temperature to a temperature that is at least 1° C. below normothermia and which decreases the patient's metabolic demand.

2. A method according to claim 1 further comprising the step of:
   g. administering an antishivering treatment to the patient.

3. A method according to claim 2 wherein the wherein the anti-shivering treatment is selected from the group of anti-shivering treatments consisting of: i) administering a therapeutically effective amount of an anti-shivering agent to the donor; ii) applying warmth to the skin of the donor and iii) administering a therapeutically effective amount of an anti-shivering agent to the donor and applying warmth to the skin of the donor.

4. A method according to claim 2 wherein the anti-shivering treatment comprises administering to the donor a therapeutically effective amount of at least one anti-shivering agent selected from the group consisting of: i) dopamine receptor antagonists; ii) dopamine receptor agonists; iii) α-opioid receptor agonists; iv) opioid agonist-antagonist analgesics, v) serotonin 5HT1a receptor agonists and vi) alpha-2 adrenergic receptor agonists.

5. A method according to claim 1 wherein the patient's body temperature is cooled to and maintained within the range of 32-34° C. while intra-aortic counterpulsation is performed.

6. A method according to claim 1 wherein the heat exchanger is positioned in a vein.

7. A method according to claim 6 wherein the heat exchanger is positioned in the vena cava.

8. A method according to claim 1 wherein both the heat exchanger and the counterpulsation balloon are positioned in the patient's aorta.

9. A method according to claim 8 wherein the heat exchanger and the counterpulsation balloon are on a single catheter which functions as both the heat exchange catheter and the balloon counterpulsation catheter.

10. A method according to claim 9 wherein the counterpulsation balloon is positioned on the catheter distal to the heat exchanger.

11. A method according to claim 9 wherein the counterpulsation balloon is positioned on the catheter provimal to the heat exchanger.

12. A method according to claim 9 wherein a single balloon functions as both the counterpulsation balloon and the heat exchanger.

13. A method according to claim 12 wherein the counterpulsation balloon is inflated with a cold gas so as to perform a heat exchange function as well as a counterpulsation function.

14. A method according to claim 1 wherein the heat exchanger comprises a metal which improves its heat exchange efficiency.

15. A method according to claim 1 wherein the heat exchanger is positioned within the patient's aortic arch and is configured so as not to block branch vessels that emanate from the aortic arch.

16. A method according to claim 15 wherein the heat exchanger comprises a plurality of separate heat exchange tubes through which heat exchange fluid circulates.

17. A method according to claim 16 wherein said plurality of separate heat exchange tubes are constructed and positioned on the catheter so as to be positionable within the aortic arch without obstructing the coronary ostia, bracheocephalic trunk, left common carotid artery or left Subclavian artery.

* * * * *